(12) United States Patent
Velasco Medina et al.

(10) Patent No.: US 10,413,609 B2
(45) Date of Patent: Sep. 17, 2019

(54) ARTIFICIAL BACTERIOPHAGE BASED ON CARBON NANOSTRUCTURES FOR SUPPLYING MEDICAMENTS

(71) Applicant: UNIVERSIDAD DEL VALLE, Cali (CO)

(72) Inventors: Jaime Velasco Medina, Cali (CO); John Michael Espinosa Durán, Cali (CO); Julio César Arce Clavijo, Cali (CO)

(73) Assignee: Universidad del Valle, Cali (CO)

( * ) Notice: Subject to any disclaimer, the term of this patent is extended or adjusted under 35 U.S.C. 154(b) by 0 days.

(21) Appl. No.: 15/517,568

(22) PCT Filed: Feb. 17, 2015

(86) PCT No.: PCT/IB2015/051144
§ 371 (c)(1),
(2) Date: Apr. 7, 2017

(87) PCT Pub. No.: WO2016/055870
PCT Pub. Date: Apr. 14, 2016

(65) Prior Publication Data
US 2017/0326239 A1    Nov. 16, 2017

(30) Foreign Application Priority Data

Oct. 10, 2014   (CO) .................................. 14-225751

(51) Int. Cl.
| | | |
|---|---|---|
| *A61K 47/06* | (2006.01) | |
| *A61K 9/51* | (2006.01) | |
| *B82Y 5/00* | (2011.01) | |
| *C01B 32/159* | (2017.01) | |
| *A61K 35/76* | (2015.01) | |
| *A61K 9/00* | (2006.01) | |
| *B82Y 15/00* | (2011.01) | |
| *B82Y 40/00* | (2011.01) | |

(52) U.S. Cl.
CPC ............ *A61K 47/06* (2013.01); *A61K 9/0019* (2013.01); *A61K 9/51* (2013.01); *A61K 9/5115* (2013.01); *A61K 35/76* (2013.01); *B82Y 5/00* (2013.01); *C01B 32/159* (2017.08); *B82Y 15/00* (2013.01); *B82Y 40/00* (2013.01)

(58) Field of Classification Search
CPC ........ A61K 47/06; A61K 9/51; A61K 9/5115; A61K 9/0019; A61K 35/76; B82Y 5/00; B82Y 15/00; B82Y 40/00; C01B 32/159
See application file for complete search history.

(56) References Cited

PUBLICATIONS

Arsawang et al., How do Carbon Nanotubes Serve as Carriers for Gemcitabine Transport in a Drug Delivery System, J. Mol. Graphics and Modeling 29:591-596 (2011).
Bottini et al., PEG-Modified Carbon Nanotubes in Biomedicine: Current Status and Challenges Ahead, Biomacromolecules 12:3381-3393 (2011).
Gangupomu and Capaldi, Interactions of Carbon nanotube with Lipid Bilayer Membranes, J. Nanomaterials 2011:1-7 (2011).
Huang et al., A New Family of Folate-decorated and Carbon Nanotube-mediated Drug Delivery System: Synthesis and Drug Delivery Response, Adv. Drug Delivery Reviews 63:1332-1339 (2011).
Ji et al., Carbon Nanotubes in Cancer Diagnosis and Therapy, Biochimica et Biophysica Acta, 1806:29-35 (2010).
Liu et al., Carbon Materials for Drug Delivery & Cancer Therapy, 14(7-8):317-323 (Jul.-Aug. 2011).
Meng et al., Single Walled Carbon Nanotubes as Drug Delivery Vehicles: Targeting Doxorubicin to Tumors, Biomaterials 33:1689-1698 (2012).
Mody et al., Dendrimer, Liposomes, Carbon Nanotubes and PLGA Nanoparticles: One Platform Assessment of Drug Delivery Potential, AAPS Pharm. Sci. Tech. 15(2):388-399 (2014).
Mousavi et al., Carbon Nanotube-Encapsulated Drug Penetration Through the Cell Membrane: An Investigation Based on Steered Molecular Dynamics Simulation, J. Membrane Biol. 246:697-704 (2013).
Nel et al., Understanding Biophysicochemical Interactions at the Nano-bio Interface, Nature Materials 8:543-557 (2009).
Rastogi et al., Carbon Nanotubes: An Emerging Drug Carrier for Targeting Cancer Cells, J. Drug Delivery 2014:1-23 (2014).
Rugnim et al., Molecular Dynamics Properties of Varying Amounts of the Anticancer Drug Gemcitabine inside and Open-ended Single-Walled Carbon Nanotube, Chem. Phys. Letters 550:99-103 (2012).
Rugnim et al., Replica Exchange Molecular Dynamics Simulation of Chitosan for Drug Delivery System Based on Carbon Nanotube, J Mol. Graphics and Modeling 39:183-192 (2013).
Vashist et al., Delivery of Drugs and Biomolecules Using Carbon Nanotubes, Carbon 49:4077-4097 (2011).
Walkey and Chan, Understanding and Controlling the Interacion of Nanomaterials with Proteins in a Physiological Enviroment, Chem. Soc. Rev. 41:2780-2799 (2012).
Wong et al., Carbon Nanotubes for Delivery of Small Molecule Drugs, Adv. Drug Delivery Reviews 65:1964-2015 (2013).
McNicholas et al., Structure and Function of Glucose Binding Protein—Single Walled Carbon Nanotube Complexes, Small Nano Micro, 2012, 1-7.
Kostarelos et al., Cellular Uptake of Functionalized Carbon Nanotubes is Independent of Functional Group and Cell Type, Nature Nanotechnology, 2007, 108-113, (2).

(Continued)

*Primary Examiner* — Robert S Cabral
(74) *Attorney, Agent, or Firm* — The Morales Law Firm; Joseph L. Morales

(57) ABSTRACT

The invention relates to an artificial bacteriophage for supplying medicaments, nutrients, proteins, DNA/RNA or other type of molecules to bacteria and/or diseased cells, directly to the cytoplasm, passing through the cell membrane thereof, through a pore of said membrane. The artificial bacteriophage is based on carbon nanostructures and comprises a nanocontainer for medicaments, a channel for transporting medicaments and a tip together with an array of linker proteins and protein receptors.

14 Claims, 6 Drawing Sheets

(56) References Cited

PUBLICATIONS

Saifuddin et al., Carbon Nanotubes: A Review on Structure and Their Interaction with Proteins, Journal of Chemistry, 2013, 1-19.
Wong et al., Carbon Nanotubes for Delivery of Small Molecule Drugs, Advanced Drug Delivery Reviews, 2013, 1964-2015 (65).
Liu et al, Supramolecular Chemistry on Water-Soluble Carbon Nanotubes for Drug Loading and Delivery, ACS Nano, 2007, 50-56 (1:1).
Li et al., Platinum (IV) Prodrugs Entrapped Within Multiwalled Carbon Nanotubes: Selective Release by Chemical Reduction and Hydrophobicity Reversal, Chem. Sci. 2012, 2083-2087 (3).
Zahra et al., Carbon Nanotube-Encapsulated Drug Penetration Through the Cell Membrane: An Investigation Based on Steered Molecular Dynamics Simulation, J. Membrane Biol., 2013 697-704 (246).
Wang and Li, Magnetic Properties of All-carbon Graphene-Fullerene Nanobuds, Phys. Chem. Chem. Phys., 2011, 13, 5945-5951.
Bhaskar and Lim, Engineering Protein Nanocages as Carriers for Biomedical Applications, NPG Asia Materials, 2017, 1-18 (9).
Montellano et al., Fullerene C60 as a Multifunctional System for Drug and Gene Delivery, Nanoscale, 2011, 4035-4041 (3).
Bhirde et al., Targeted Killing of Cancer Cells in Vivo and in Vitro with EGF-Directed Carbon Nanotube-Based Drug Delivery, ACS Nano, 2009, 307-316 (3:2).
Oliveira et al., Protein Functionalized Carbon Nanomaterials for Biomedical Applications, Carbon, 2015, 767-779 (95).
Chen et al., Noncovalent Functionalization of Carbon Nanotubes for Highly Specific Electronic Biosensors, PNAS, 2003, 4984-4989 100(9).
Liu et al., siRNA Delivery into Human T Cells and Primary Cells with Carbon-Nanotube Transporters, Nanobiotechnology, 2007, 2023-2027 (46).
Spicer and Davis, Selective Chemical Protein Modification, Nature Communications, 2014, 1-14.
Lewandowski et al., Sequence-Specific Peptide Synthesis by an Artificial Small-Molecule Machine, Science, 2013, 189-194 (339).
Shi and Gan, Open-Cage Fullerenes as Tailor-Made Container for a Single Water Molecule, J. Phys. Org. Chem., 2013, 766-772 (26).
Ortega-Guerrero et al., TRPV1 Channel as a Target for Cancer Therapy Using CNT-based Drug Delivery Systems, Biophysics in Europe, 2016, 1-11.

ARTIFICIAL BACTERIOPHAGE BASED ON CARBON NANOSTRUCTURES FOR SUPPLYING MEDICAMENTS

OBJECT OF THE INVENTION

This invention patent request refers to an artificial bacteriophage constructed based on carbon nanostructures for controlled and localized drug delivery at cellular level, seeking to inject medications or other substances into sick cells or pathogenic organisms to cure or destroy them. Thus, keeping said medication from also affecting healthy cells or certain unwanted parts of the body, given that the drug could be transported by the bodily fluids to these parts, triggering secondary effects in patients, like hair loss, vomit, headache, weight loss, extreme pain, among others; and causing other diseases, like kidney failure, heart failure, hypertension, osteoporosis, and blindness among others. All this worsens the patients' quality of life and—in some cases—may cause their death.

BACKGROUND OF THE INVENTION

Within the state of the technique, we find progress in nanotechnology. Currently, in this area of science it is possible to develop nano systems for controlled and localized drug delivery at cellular scale. These systems are known as drug delivery nano systems (DDNS), like liposomes, dendrimers, and micelles, among others, which permit reducing significantly secondary effects in patients when the respective medical treatment is taking place.

However, even when the drug supply is highly selective and control of the drug release is precise, in the DDNS developed until now, the drug may be released in the extracellular medium. When this occurs, the medication acts not only on target sick cells or pathogenic organisms, but also on healthy cells or unwanted parts of the body because the bodily fluids can transport the drug, producing secondary effects. In other DDNS, it can be guaranteed that the drug is released only in the intracellular medium, but it cannot be guaranteed that the DDNS will be introduced satisfactorily into the cytosol (liquid part of the cell cytoplasm), reducing the drug's effectiveness. It is worth stating that existing DDNS are quite primitive in the sense that they have no motion mechanism and lack intelligence. These DDNS travel through the blood or any bodily fluid guided by the direction of the fluid or Brownian motion (random motion observed in some microscopic particles found in a fluid).

Hence, the idea is that of designing and manufacturing bionanorobots capable of traveling inside the human body and transporting medications to cure or destroy sick cells or any type of pathogenic organism. These bionanorobots could have their own motion mechanism, such as a flagellate (moving appendage with whip shape), a turbine, or even motor systems with wheels, as well as detection mechanisms (bionanosensors) based on DNA, carbon nanotube heterostructures, proteins, selective surfaces, or simple electrochemical detection; and a drug release system, such as a medication pump, or gate-controlled drug repository. Clearly, bionanorobots also need a specific system to generate energy, and process and communicate information. These bionanorobots can originate from or can be based on modified biological systems, on completely artificial systems, or a combination of these; however, although bionanorobots are quite promising, their design is a very difficult task. This is because bionanorobots are comprised of nanomachines and their design depends on the operation or function to implement artificially or on the profound knowledge of the biological model used as guide or inspiration.

Considering the aforementioned and based on the lambda λ bacteriophage (bacteriophage virus that infects the *Escherichia Coli* bacteria, discovered in 1950), which has a specialized system to inject DNA through the cellular membrane, this request introduces the design, along with its characteristic construction techniques, of an artificial bacteriophage properly conceived, using carbon nanostructures for drug delivery and/or sample collection.

The artificial bacteriophage was conceived through corresponding research and modeled with several design tools; among these are the Nanoengineer-1 software, the Gromacs software for molecular dynamics simulations using both Gromos force fields 53 to 6 and OPLS-AA and, lastly, the Lammps software, using the Dreiding force field. The simulations were carried out at 310 K at 1 atm pressure, in an air and water environment.

Within the state of the technique, we find multiple bacteriophages with several structural construction configurations from nanosystems and nanoparticles grouped amongst themselves; said structures have been achieved due to progress in science and, specifically, in nanotechnology.

As noted in US invention patent, U.S. Pat. No. 5,864,013 (Jan. 26, 1999), requested by Nanoframe, LLC, [US], describing an invention patent, which consists of providing materials to produce nanometric structures for their respective use.

The WIPO invention patent, WO0077196 (Dec. 21, 2000), requested by Goldberg Edward, B [US], describes a gene and its protein sequences of gene 35 of a T4 bacteriophage.

The US invention patent, US 20140186265 (Jul. 3, 2014), requested by Colorado State University Research Foundation [US], describes a multifunctional bacteriophage to supply therapeutic agents and image formation reagents.

The WIPO invention patent, WO201430020 (Nov. 11, 2007), requested by the University of Leicester [GB], describes therapeutic bacteriophages.

The European invention patent, EP 26533536 (Oct. 23, 2013), requested by Iris, Francois [FR], describes a preparation process of bacteriophages modified by inserting random sequences in the proteins focalized in the bacteriophages.

GENERAL AND DETAILED DESCRIPTION OF THE INVENTION

The technical problem targeted by this request consists of that drug supply at cellular level should not affect healthy cells or undesired parts of the body, where bodily fluids could transport the drug. The aim is to reduce inasmuch as possible secondary effects in patients, like hair loss, vomit, headache, weight loss, extreme pain, among others, as well as avoid the onset of diseases, like kidney failure, heart failure, hypertension, osteoporosis, and blindness among others.

The present invention patent seeks to contribute with a solution to the problem through an artificial bacteriophage to supply medications, nutrients, proteins, DNA/RNA or other types of molecules to the sick cells and/or bacteria, directly on the cytoplasm, passing through its cellular membrane via a pore of said membrane.

The artificial bacteriophage (1), based on carbon nanostructures, is made up of the following structural components: a medication nanocontainer (2) of icosahedral shape elaborated through a carbon, fullerene structure, which can have a diameter between 4.0 and 10 nm (a); a drug transport channel (3) elaborated through a single-wall carbon nanotube (SWCNT) or multi-wall carbon nanotube (MWCNT), which can have a diameter between 2.0 and 3.5 nm (b) and a length between 10 and 20 nm (c); and a tip or pinnacle (4) elaborated through an SWCNT/MWCNT segment or boron nitride SWCNT heterostructure with a diameter between 2.0 and 3.5 nm (d) and an average total length of 5.0 nm (e), functionalized with a binding protein array (linkers) (4a) and protein receptors (4.b), 0.3 nm thick and average total length of 2.0 nm (f) (FIGS. 1 and 1A).

In the lower end of the drug transport channel (3) we find the pinnacle (4), comprised of an SWCNT/MWCNT segment or a boron nitride SWCNT heterostructure (4a), and a binding protein array (linkers) (4b) and protein receptors (4c). Protein receptors (4c) are complementary proteins to the proteins around certain pores of the cellular membrane of the sick cells or pathogenic organisms used to locate the pore and adhere to them. The artificial bacteriophage uses said pore to inject directly the medications or other substances in the cytoplasm of target organisms.

The binding proteins (linkers) (4b) are necessary because the protein receptors (4c) are not chemically related to the SWCNT/MWCNT (4a); besides the binding protein array (4b) adopts a ring shape around the nanotube tip, allowing the pinnacle (4) of the artificial bacteriophage (1) to have greater stability for effective translocation of medications and others. Based on the aforementioned, three pinnacle designs were proposed (4) with the following configurations: SWCNT along with binding proteins and protein receptors (5); boron nitride SWCNT heterostructure along with binding proteins and protein receptors (6); and a boron nitride protein—SWCNT heterostructure with binding proteins and protein receptors (7) (FIG. 2).

The first pinnacle design (5) consists of an SWCNT segment (4a) with a binding protein array (4b) and protein receptors (4c). This pinnacle has a diameter between 2.0 and 3.5 nm (d) and an average total length of 5 nm (3 nm (e) plus 2 nm (f)). The pinnacle configuration (4) consists of a binding protein array (4b) with ring shape (4.1b) around the lower end of the SWCNT segment (4a), giving stability to the tip and permitting control of drug release. This ring (4.1b) is 0.8 nm long and 0.3 nm thick. The protein receptors (4c) are 1.2 nm long and 0.3 nm thick, approximately (FIG. 2A).

The second pinnacle design (6) consists of a boron nitride SWCNT heterostructure (6a) along with a binding protein array (4b) and protein receptors (4c). This pinnacle has a diameter between 2.0 and 3.5 nm (d) and an average total length of 5 nm (3 nm (e) plus 2 nm (f)). The pinnacle configuration (4) consists of a binding protein array (4b) with ring shape (4.1b) around the lower end of the boron nitride SWCNT heterostructure (6a), giving stability to the tip and permitting control of drug release. The boron nitride SWCNT heterostructure (6a) is comprised of three segments (6b, 6c, 6d) where each segment is 1.0 nm long. Four rings form each segment, two rings are of boron nitride and the other two are SWCNT. The ring of binding proteins (4.1b) is 0.8 nm long and 0.3 nm thick. The protein receptors (4c) are 1.2 nm long and 0.3 nm thick, approximately (FIG. 2B).

The third pinnacle design (7) consists of a boron nitride protein—SWCNT heterostructure (7a) along with a binding protein array (4b) and protein receptors (4c). This pinnacle has a diameter between 2.0 and 3.5 nm (d) and an average total length of 5 nm (3 nm (e) plus 2 nm (f)). The pinnacle configuration (4) consists of a binding protein array (4b) with ring shape (4.1b) around the lower end of the boron nitride proteins—SWCNT heterostructure (7a), giving stability to the tip and permitting control of drug release. The boron nitride proteins—SWCNT heterostructure (7a) is made up of three segments (7b, 7c, 7d) with binding proteins (4b) covalently functionalized outside of the boron nitride SWCNT heterostructure. Each segment (7b, 7c, 7d) is 1.0 nm thick, formed by four rings, two rings are of boron nitride and the other two are SWCNT, with a ring of binding proteins around the last ring of SWCNT. The ring of binding proteins (4.1b) located on the pinnacle tip is 0.8 nm long and 0.3 nm thick. The protein receptors (4c) are 1.2 nm long and 0.3 nm thick, approximately (FIG. 2C).

Placement of the binding proteins (4b) and protein receptors (4c) in the lower end of the pinnacles (5, 6, 7) is the same in the three designs. The pinnacle designs (4) permit performing the same function of a valve, which permits maintaining high hydrostatic pressure or high ionic potential within the bacteriophage (1) and controlling drug release during the indicated moment. The pinnacle (4) can be controlled through a voltage; using molecules similar to rotaxane or through allosteric control of the protein receptors (4c) employing proteins similar to those of the Lambda bacteriophage or the type-III secretion system of the Gram negative bacteria. In case of using voltage, two possibilities exist, voltage can be an external potential applied during medical treatment or can be generated due to the interaction with the cellular membrane. To carry out allosteric control, it is produced by the interaction of the protein receptors (4c) with cellular membrane proteins located around the pore used to inject the medication, which produces a structural change in said receptors (4c) and in binding proteins (4b), thus, activating the pinnacle (4) for drug release.

The artificial bacteriophage's (1) function is that of supplying medications or other molecules in controlled and localized manner to treat diseases whose pharmacological treatment has very harmful secondary health effects, as in the case of cancer. The results obtained for the artificial bacteriophage (1) are shown through molecular dynamic simulations where medications, like doxorubicin, geldanamycin, methotrexate, gemcitabine, or proteins with antibacterial properties, like 1MV2 and 1MV5, can be stored in the nanocontainer (2) and flow through the transport channel (3) in water or in an ionic solution, demonstrating the correct assembly and operation of the artificial bacteriophage (1) (FIG. 3).

Based on that described, the content within the artificial bacteriophage (1) can be water or an ionic solution, usually sodium chloride (NaCl), so that the concentration inside the artificial bacteriophage (1) is higher than in the sick cells or target organisms, with the purpose of producing an ionic potential gradient that guides the medication flow. In case of only using water, the hydrostatic pressure inside the artificial bacteriophage (1) must be higher than in the target organisms, thus, the pressure gradient guides the medication flow.

FIG. 3 shows several instantaneous images of the results of molecular dynamic simulation of the artificial bacteriophage (1) for some medications flowing through the transport channel. These tests included vacuum, air, and water as simulation environment, where water served to emulate blood plasma because plasma is 75% water. Through these simulations, we began with the medication in water at high pressure in the nanocontainer, observing how a hydrostatic pressure gradient guides drug transport through the transport channel for its subsequent release. The simulations revealed how the medications are driven by the water flow and that because of their hydrophobic characteristics they are partially absorbed by the walls of the transport channel (3).

To inject medications in the cells, the artificial bacteriophage (1) uses certain ionic transport channels present in cell membranes. These cation channels are present in several types of carcinogenic cells and permit passage of small molecules of similar molecular weight as that of the medications studied. In this case, the following procedure supplies drugs to the sick cell or bacteria: 1) locate the proteins close to the pore by using protein receptors (4c) from the pinnacle (4); 2) apply a stimulus (voltage or ligand) to activate the pinnacle (4) and permit drug release; 3) drug supply through hydrostatic pressure gradient or ionic potential gradient, thus, achieving localized drug release, minimizing inasmuch as possible collateral effects on the patient treated.

Figure 1:
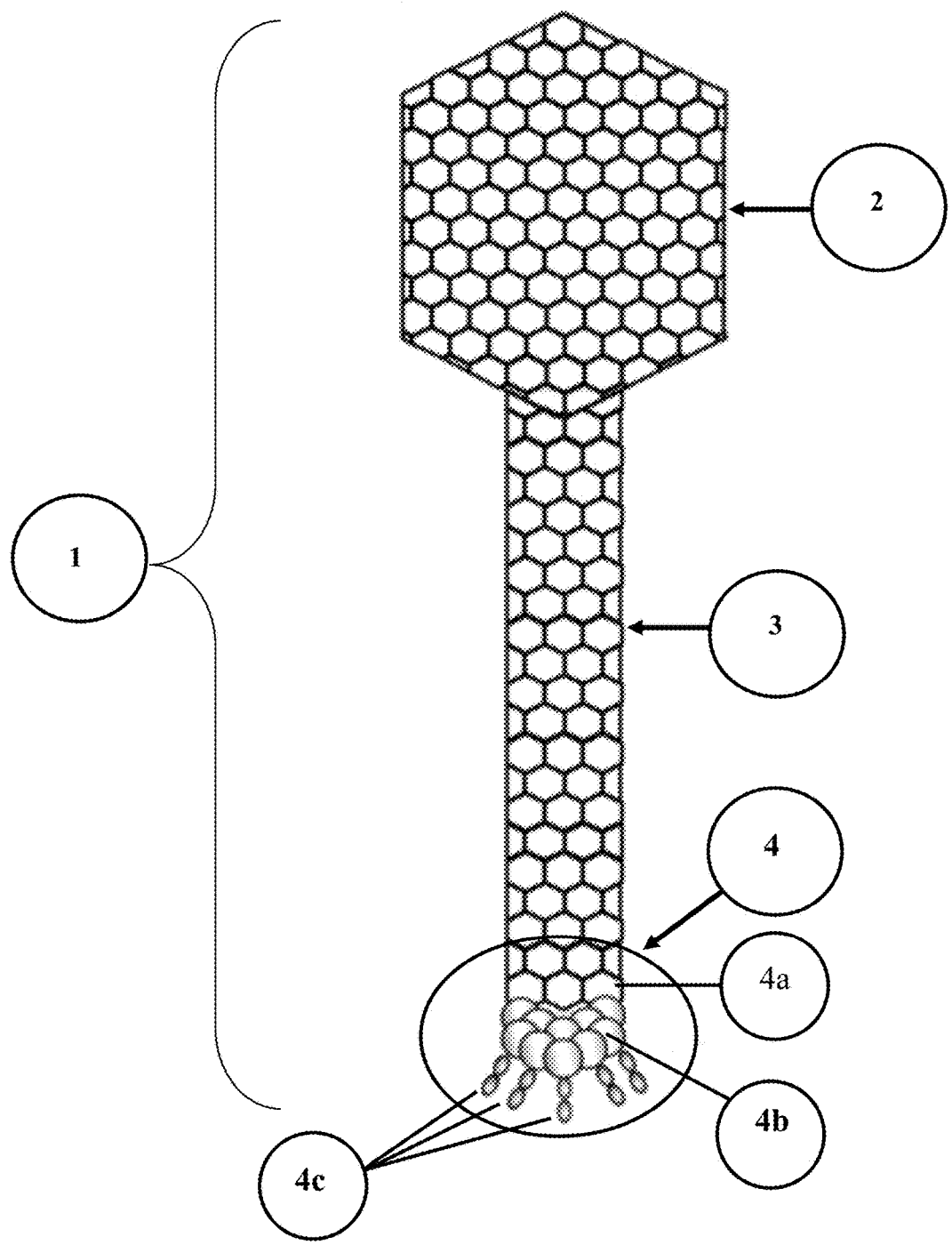
FIG. 1. Shows an artificial bacteriophage (1) based on carbon nanostructures along with its characteristic construction techniques.
Figure 1A:
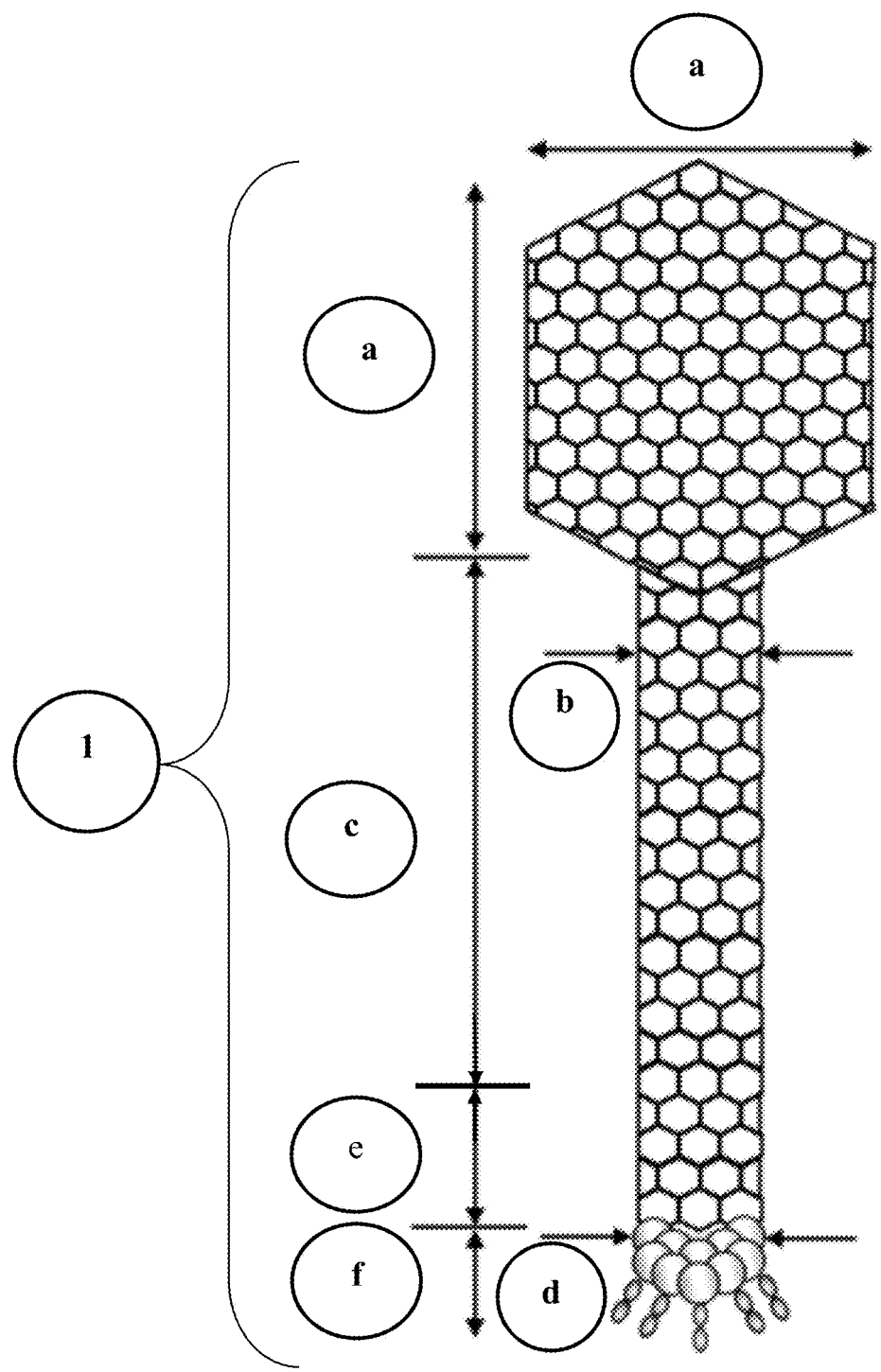
FIG. 1A. Shows an artificial bacteriophage (1) along with its dimensions designated under representation in letters.
Figure 2:
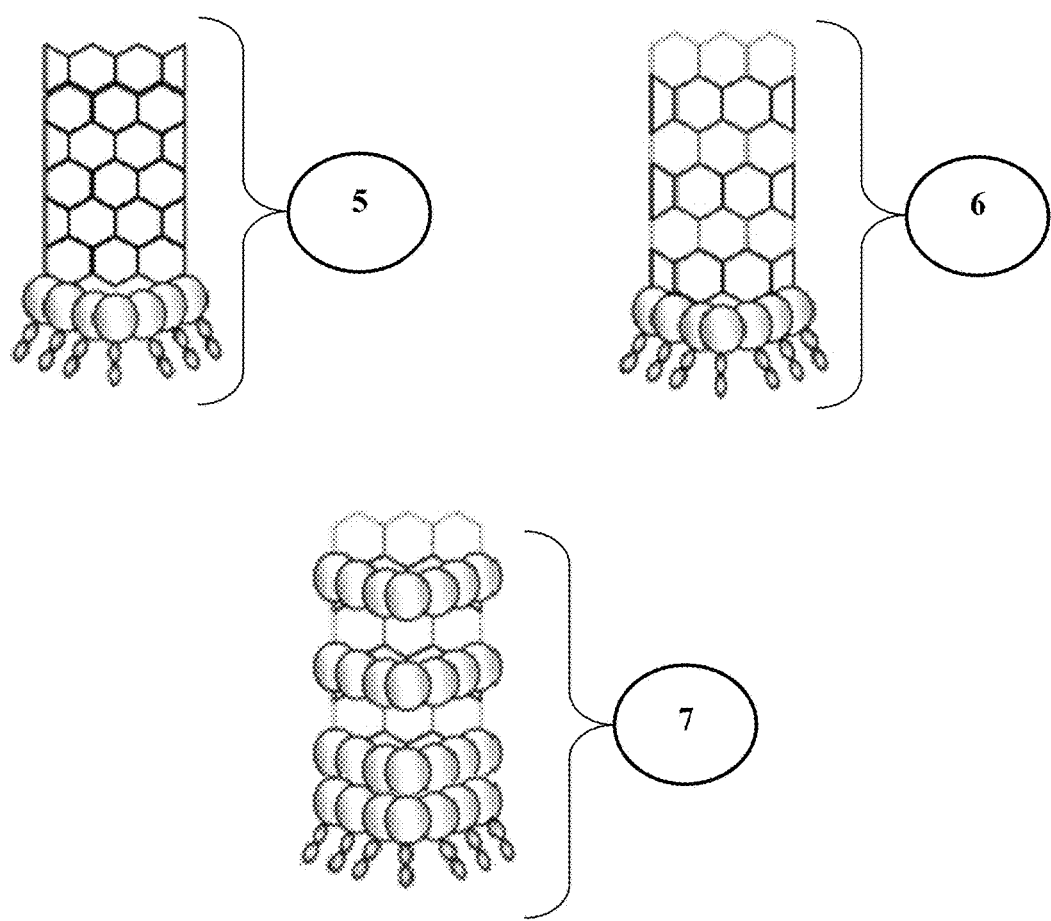
FIG. 2. Shows different pinnacle models (4) that are part of an artificial bacteriophage (1) along with its respective hetero-structures and binding protein arrays (4b) and protein receptors (4c), as well as with its characteristic construction techniques.
Figure 2A:
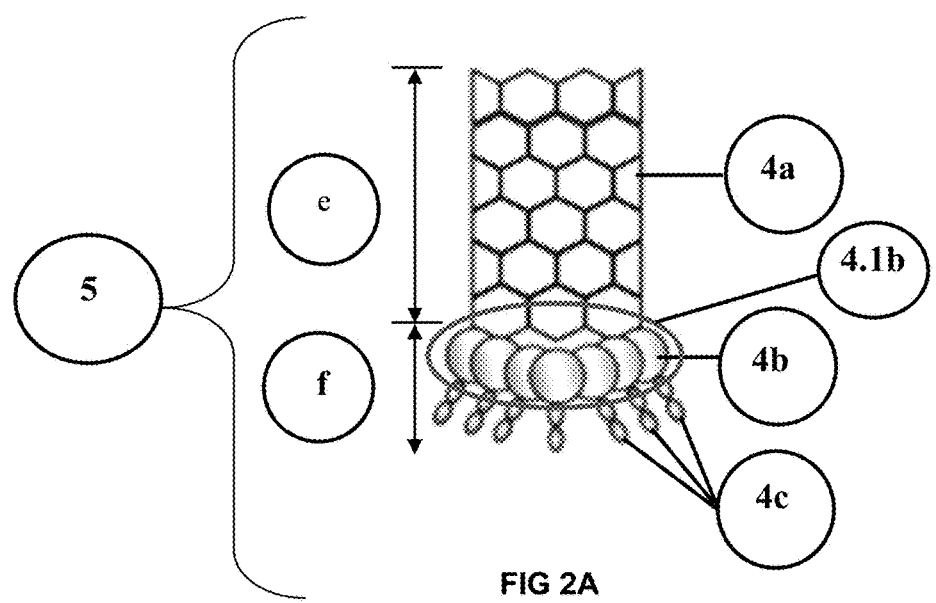
FIG. 2A. Shows an artificial bacteriophage (1) with the first pinnacle model (4) along with its respective binding protein array (4a) and protein receptors (5), as well as with its characteristic construction techniques and dimensions designated under representation in letters.
Figure 2B:
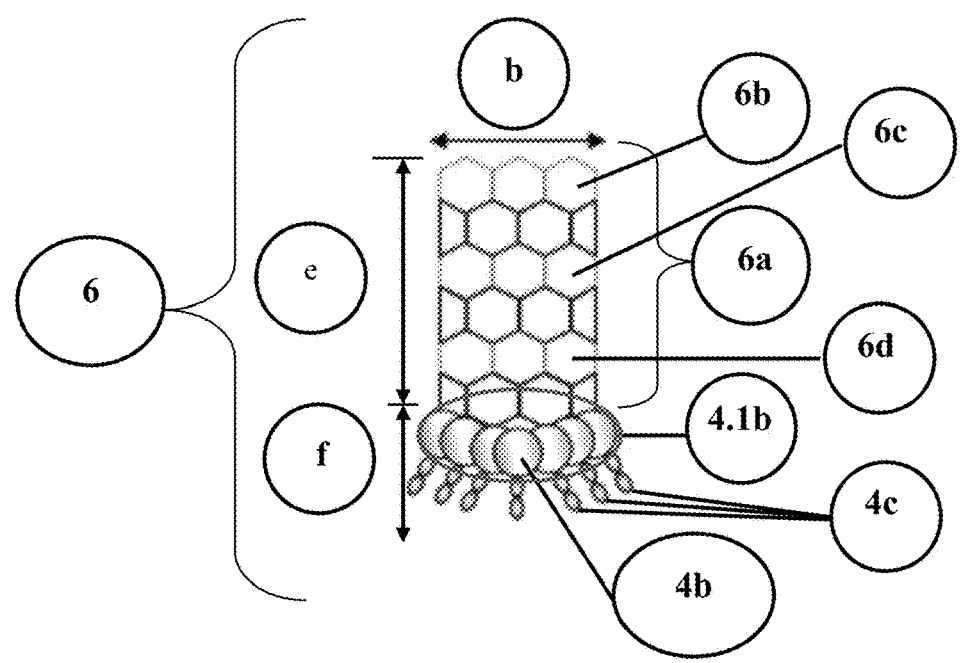
FIG. 2B. Shows an artificial bacteriophage (1) with the second pinnacle model (4) along with its respective binding protein array (4b) and protein receptors (4c), as well as with its characteristic construction techniques and dimensions designated under representation in letters.
Figure 2C:
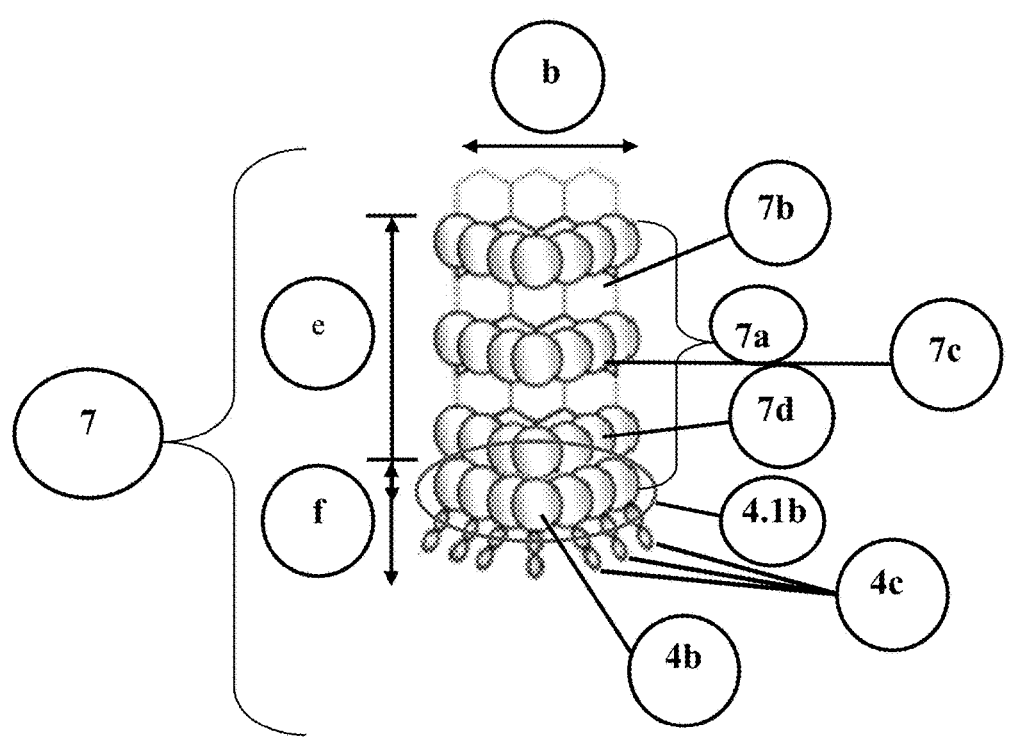
FIG. 2C. Shows an artificial bacteriophage (1) with the third pinnacle model (4) along with its respective binding protein array (4b) and protein receptors (4c), as well as with its characteristic construction techniques and dimensions designated under representation in letters.
Figure 3:
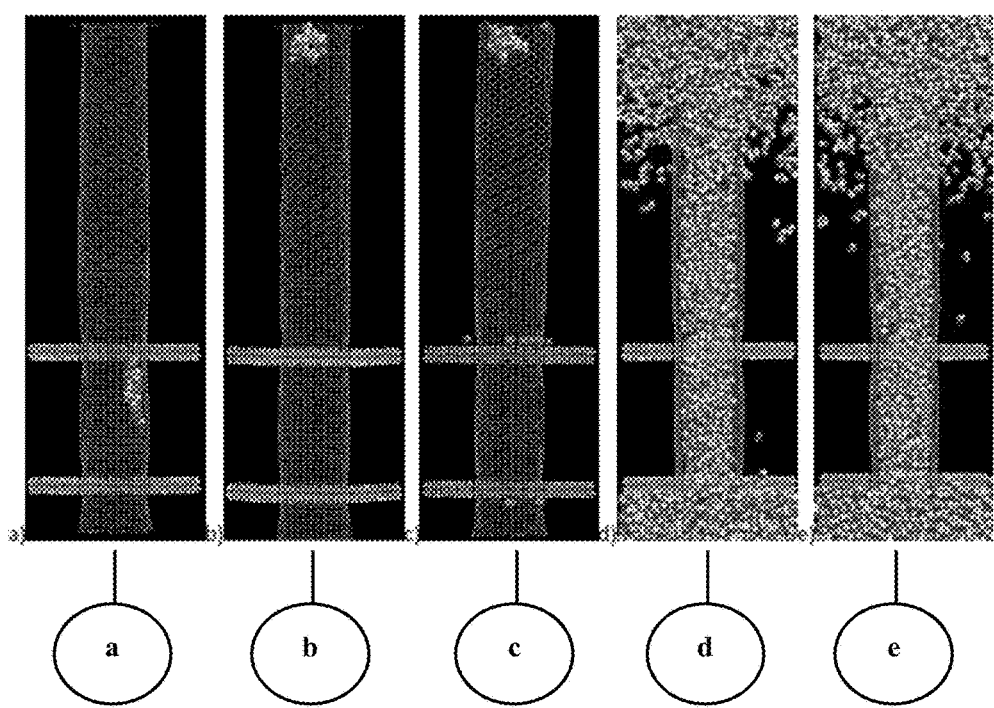
FIG. 3. Presents a graphic of several simulation images of an artificial bacteriophage (1), showing drug transport in several environments through the transport channel (3) elaborated from a single-wall carbon nanotube (SWCNT). In vacuum environment, it shows image a) methotrexate and b) geldanamycin. In air environment, it shows image c) geldanamycin. In water environment, it shows image d) gemcitabine and e) doxorubicin.

The invention claimed is:

1. An artificial bacteriophage, comprising:
a) a medication nanocontainer with an icosahedral shape having a Fullerene carbon structure; connected to
b) a single-wall carbon nanotube (SWCNT) having a drug transport channel, said SWCNT is located on one end of said medication nanocontainer; and
c) wherein said drug transport channel ends at a pinnacle having a SWCNT or a boron nitride SWCNT heterostructure, a binding protein array, and protein receptors.

2. The artificial bacteriophage based on carbon nanostructures, according to claim 1, wherein the medication nanocontainer has a diameter between 3 and 10 nm.

3. The artificial bacteriophage based on carbon nanostructures, according to claim 1, wherein the drug transport channel has a diameter between 2 and 3.5 nm, and a length between 10 and 20 nm; can be of armchair-type or zigzag, and have different chiralities.

4. The artificial bacteriophage based on carbon nanostructures, according to claim 1, wherein the pinnacle has a diameter between 2 and 3.5 nm, and an average length of 5 nm.

5. The artificial bacteriophage based on carbon nanostructures, according to claim 1, wherein the binding proteins array is 0.8 nm long and 0.3 nm wide, approximately.

6. The artificial bacteriophage based on carbon nanostructures, according to claim 1, wherein the protein receptors are 1.2 nm long, and 0.3 nm thick, approximately.

7. The artificial bacteriophage based on carbon nanostructures, according to claim 1, wherein the pinnacle consists of a boron nitride SWCNT heterostructure divided into three segments.

8. The artificial bacteriophage based on carbon nanostructures, according to claim 7, the protein array is 0.8 nm long and 0.3 nm wide, approximately.

9. The artificial bacteriophage based on carbon nanostructures, according to claim 7, wherein each segment of the boron nitride SWCNT heterostructure is 1.0 nm thick, approximately.

10. The artificial bacteriophage based on carbon nanostructures, according to claim 7, wherein the protein array is 0.8 nm long and the protein receptors are 1.2 nm long and 0.3 nm thick.

11. The artificial bacteriophage based on carbon nanostructures, according to claim 1, wherein the pinnacle consists of a boron nitride protein SWCNT heterostructure, and where the binding protein array comprises binding proteins covalently functionalized outside the boron nitride SWCNT heterostructure.

12. The artificial bacteriophage based on carbon nanostructures, according to claim 11, characterized because wherein said boron nitride protein—SWCNT heterostructure has a plurality of segments and wherein each segment of the boron nitride SWCNT heterostructure is 1.0 nm thick.

13. The artificial bacteriophage based on carbon nanostructures, according to claim 11, wherein the binding protein array is 0.8 nm long and the protein receptors (5) are 1.2 nm long and 0.3 nm thick, approximately.

14. The artificial bacteriophage based on carbon nanostructures, according to claim 1, wherein a procedure for drug delivery through the artificial bacteriophage comprises the stages of: a) location and adhesion to the proteins around the membrane pore of the sick cell or bacteria; b) applies a stimulus (voltage) or self-stimulus (ligand) appropriate to activate drug release; c) supplies the medication through osmotic pressure gradient or ionic potential gradient.

* * * * *